United States Patent [19]

Snider

[11] Patent Number: 5,336,498
[45] Date of Patent: Aug. 9, 1994

[54] METHOD AND APPARATUS FOR ALLEVIATING BACK PAIN

[76] Inventor: Max H. Snider, 68 Harrington Crescent, Willowdale, Ontario, M2M 2Y5, Canada

[21] Appl. No.: 706,973

[22] Filed: May 29, 1991

[51] Int. Cl.⁵ ............................................. A01N 25/34
[52] U.S. Cl. ....................................... 424/402; 5/632; 5/636; 5/646; 606/240
[58] Field of Search .......................... 5/632, 636, 646; 606/240; 424/402

[56] References Cited

U.S. PATENT DOCUMENTS

| | | | |
|---|---|---|---|
| 4,114,612 | 9/1978 | Benjamin | 5/636 |
| 5,033,137 | 7/1991 | Pedrow | 5/636 |

*Primary Examiner*—Thurman K. Page
*Assistant Examiner*—William E. Benston

[57] ABSTRACT

The invention disclosed comprises apparatus in the nature of resiliently flexible laminated pads, with or without magnetic tape, used to apply pressure to various areas of a human body, particularly the back, to alleviate back pain and related symptoms due to muscle strain, tension or nerve irritation, as well as headaches and menstrual discomfort.

4 Claims, 4 Drawing Sheets

METHOD AND APPARATUS FOR ALLEVIATING BACK PAIN

BACKGROUND OF THE INVENTION

This invention relates to methods and apparatus for the relief of back pain and tension headaches suffered by human beings. In particular, it relates to the design of pressure pads and methods of using them to apply pressure to various areas of the human body to relieve or reduce back pain or headache.

Many human beings suffer from back pain and tension headaches. These symptoms typically occur from muscle tension, fatigue, arthritis, curvature of the spine, minor spinal disc compression, pinched nerves, strained or sprained muscles, menstrual cycle and nervous tension.

Some of these problems may be treated by light medically prescribed exercise to at least reduce back problems. Use of the present invention combined with proper exercise is a faster method of back pain relief.

It should, of course, be realized that whenever severe back pain occurs, one should always seek prompt medical diagnosis since the cause of the pain may be due to serious physical injury or ailment (such as broken ribs, torn or cut muscles, tissue or ligaments, kidney problems, herniated or severely degenerated discs, osteoporosis, tumors, etc.) and using the methods herein described, may be harmful. Whenever symptoms are due to muscle strain or sprain, it is generally advisable to apply a cold substance such as an ice pack initially to reduce swelling and then to use the present invention. When minor pain is dealt with in its early stages, recovery time is greatly reduced and further escalation to serious back damage may be averted.

If someone suffers from osteoporosis (brittle bones), they should not use these pads without professional medical advice.

SUMMARY OF THE INVENTION

The foregoing objectives and advantages are achieved by means of the present invention by the application of pads so as to apply pressure to certain parts of the body, principally when lying on or sitting against them.

The application of pressure by means of the pads disclosed herein will relax muscle tension and relieve the symptoms of pinched nerves and other symptoms according to the locations where the pressure is applied.

Ideally, in accordance with this invention, the pressure is applied by selecting one of three pads, each comprised of a base layer and a middle layer of semi-rigid but compressible materials such as synthetic foam, felt, rubber etc. and a top layer of flexible magnetic tape material.

DESCRIPTION OF THE DRAWINGS

The invention may be better understood by a description of specific embodiments thereof with reference to the attached drawings in which.

DESCRIPTION OF THE PREFERRED EMBODIMENT

Figure 1:
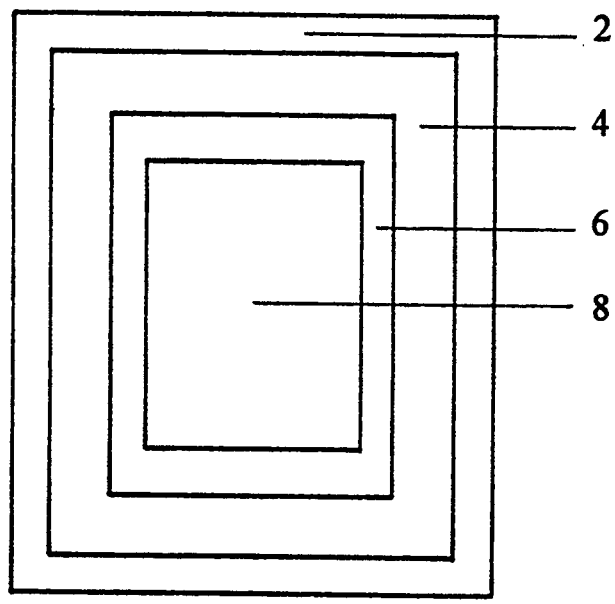
FIG. 1 is a top view of pad A.
Figure 2:
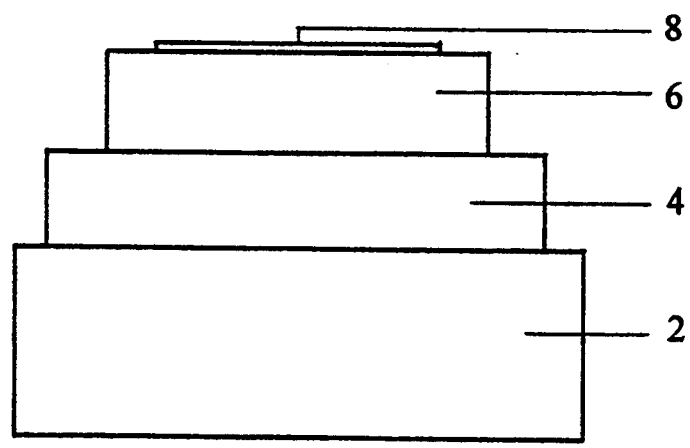
FIG. 2 is a side elevation view of pad A.

FIG. 1 and 2 show the structure of pad A which consists of a base layer (2) of resiliently compressible or elastic material such as synthetic polymer foam measuring 3 inches by 2¾ inches by 1 inch thick, and a middle layer (4) Of foam, felt or rubber material 2½ inches by 2¼ inches by ½ inch thick, and a third layer (6) of foam or felt material measuring 2 inches by 1½ inches by ½ inches thick, and a top layer (8) of flexible vinyl magnetic tape, 1½ inches by 1¼ inches by 0.03 inches thick.

Figure 3:
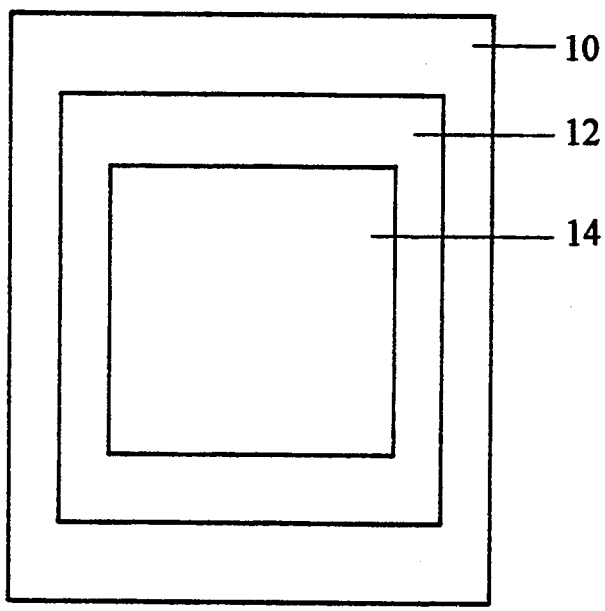
FIG. 3 is a top view of pad B.
Figure 4:
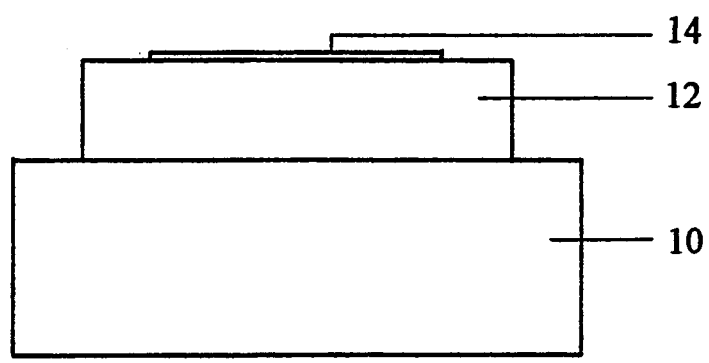
FIG. 4 is a side elevation view of pad B.

FIGS. 3 and 4 show the structure of a second version, referred to as pad B. The base (10) is made of two pound density synthetic polymer foam measuring 3 inches by 2¾ inches by 1 inch thick. The middle layer (12) is made of wool felt or foam and measures 2 inches by 2 inches by ½ inch thick. The top layer (14) is a vinyl magnetic tape measuring 1½ inches by 1½ inches and approximately 0.03 inches thick.

Figure 5:
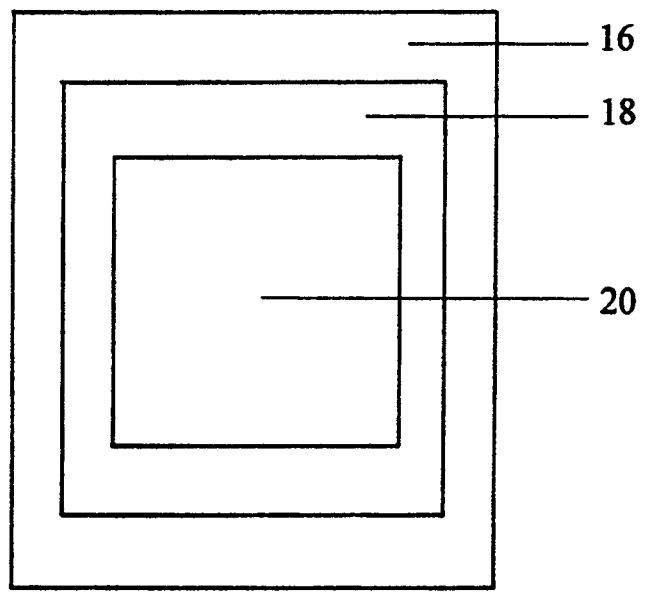
FIG. 5 is a top view of pad C.
Figure 6:
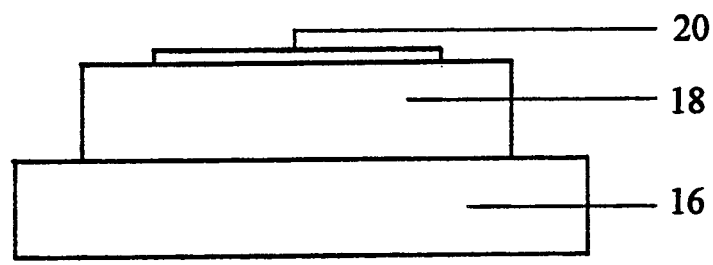
FIG. 6 is a side elevation view of pad C.

FIGS. 5 and 6 illustrate a third pad C. The base (16) is made of the same foam as the other pads and measures 3 inches by 2¾ inches by ½ inch thick. The middle layer (18) is made of felt or foam or rubber and measures 2½ inches by 2¼ inches by ½ inch thick. The top layer is vinyl magnetic tape measuring 1½ inches by 1½ inches by 0.03 inches thick.

The various layers are bonded together by using a suitable flexible adhesive and the entire pad is preferably covered by an elasticized cotton jacket to which a string or handle may be attached in order to allow the user to place the pad with ease when sitting.

Although an economical form of the pad may be made without the magnetic tape, it is felt that the magnetic tape has a balanced pressure distribution effect on muscles which are strained or tense or in spasm.

As mentioned before, whenever muscles are strained or sprained, it is advisable to promptly apply a cold article such as an ice pack for ten or fifteen minutes to keep the swelling down before any further relief is applied.

Figure 7:
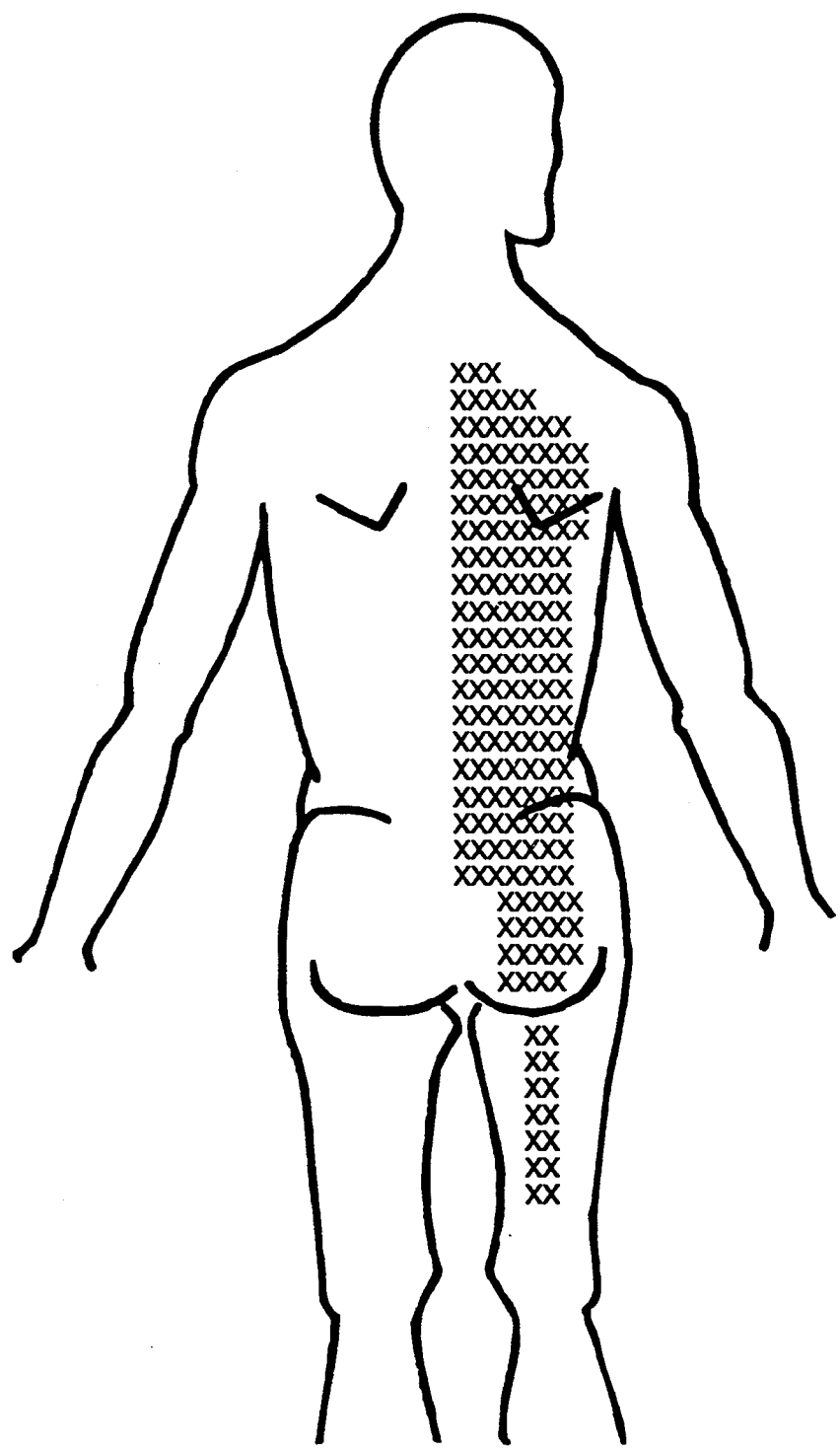
FIG. 7 is a chart showing locations of application of the pressure pad on the human body for various ailments.

The pads described may be used to alleviate muscle and nerve pain and muscle tension headaches. Specifically, the pad may be placed against painful locations or "compatibly targeted" areas on the user's back. The user can then lie on it in bed or sit against it using the back of a chair or car or truck seat when driving, in order to apply pressure to that location on the user's back. The exact location will vary and may require some movement and adjustment of the pad to find the location which is effective for the particular person or the particular symptom involved. The location for various frequently occurring symptoms is illustrated in the diagram which is FIG. 7.

The pressure and the resulting stimulation at the appropriate area of the user's back, combined with the massaging action caused by the user's natural breathing motion, will activate and direct the body's own healing resources to the problem. The user may then move or adjust the pad slightly until the exact spot where the pressure attacks the discomfort is located. The correct placement of the pads can create a slight spinal adjustment relieving pressure caused by mildly displaced or misaligned spinal vertebrae, or slightly bulging discs, thus relieving pain from pinched or irritated nerves.

The pad should be periodically moved around to find other compatibly comforting locations in order to allow good blood circulation and obtain maximum results.

Generally, first, the pad B should be applied with the smaller area towards the body but if the pressure is felt to be too great it may be turned over so that the larger contact area is pressing against the body. If there is still too much pressure, the user should change to the thinner pad C. Experience has shown that in dealing with severely knotted muscles, using the thickest pad A to supply maximum pressure and stimulation to the affected locations is advisable. Because of the thickness and high pressure of the pad A, it should be placed against a soft surface to avoid bruising. Pad A should not be used against the spine without soft backing. When applying any of the pads, it is advisable to leave it in place for about two minutes before trying another location as it takes a moment for any discomfort caused by the pad to ease and comfort to begin.

Of course, any relaxation of the mind and body which accompanies the use of the pads will be beneficial.

When the greatest discomfort has eased, it is advisable to switch to one of the thinner pads to maintain comfort with less pressure. Sleeping with the thinnest pad C under the small of the back may help avoid morning chronic back stiffness and muscle ache.

It will, of course, be realized that modifications and variations of the method and apparatus described above may be employed without departing from the inventive concept herein.

I claim:

1. A pad for self application of pressure to specific areas of one's own body comprising:
   a top layer of vinyl-magnetic tape measuring $1\frac{1}{2}$ inches by $1\frac{1}{2}$ by 0.03 inches thick,
   a middle layer of resiliently flexible polymer foam, wool felt or rubber material measuring $2\frac{1}{4}$ inches by $2\frac{1}{4}$ inches by $\frac{1}{2}$ inch thick,
   1 base layer of resiliently flexible synthetic polymer foam measuring 3 inches by $2\frac{3}{4}$ inches by $\frac{1}{2}$ inch thick.

2. A pad for self application of pressure to specific areas of one's own body comprising:
   a top layer of vinyl-magnetic tape measuring $1\frac{1}{2}$ inches by $1\frac{1}{2}$ inches by 0.03 inches thick,
   a middle layer of resiliently flexible polymer foam, wool felt or rubber material measuring 2 inches by 2 inches by $\frac{1}{2}$ inch thick,
   a base layer of resiliently flexible synthetic polymer foam measuring 3 inches by $2\frac{3}{4}$ inches by 1 inch thick.

3. A pad for self application of pressure to specific areas of one's own body comprising:
   a top layer of vinyl-magnetic tape measuring $1\frac{1}{2}$ inches by $1\frac{1}{4}$ inches by 0.03 inches thick,
   a middle layer of resiliently flexible polymer foam, wool felt or rubber material measuring $2\frac{1}{4}$ inches by $2\frac{1}{4}$ inches by $\frac{1}{2}$ inch thick,
   a base layer of resiliently flexible synthetic polymer foam measuring 3 inches by $2\frac{3}{4}$ inches by 1 inch thick,
   An intermediate third layer of resiliently flexible synthetic polymer foam, wool, felt or rubber material measuring 2 inches by $1\frac{1}{2}$ inches by $\frac{1}{2}$ inch thick.

4. A method whereby a human compresses either surface side of one of the three different thickness pads as defined in claims 1, 2 and 3, directly against the pain, by sandwiching said pad between his or her back, spinal vertebrae, buttock or hamstring muscle and the seat or back of a chair or the surface of a bed and tries the 3 pads, one at a time, using his or her own instant pain reduction as a guide to determine which pad and surface side is most effective.

* * * * *